United States Patent [19]

Gresham et al.

[11] Patent Number: 5,225,531
[45] Date of Patent: Jul. 6, 1993

[54] HEXAPEPTIDE LYS GLY ALA GLY ASP VAL

[75] Inventors: Hattie D. Gresham, Columbia; Steven P. Adams, St. Charles; Eric J. Brown, St. Louis, all of Mo.

[73] Assignee: Washington University, St. Louis, Mo.

[21] Appl. No.: 866,678

[22] Filed: Apr. 9, 1992

[51] Int. Cl.$^5$ ................................................ C07K 7/06
[52] U.S. Cl. ..................................................... 530/329
[58] Field of Search ........................... 530/329; 514/17

[56] References Cited

U.S. PATENT DOCUMENTS 5,057,604  10/1991  Brown ................................. 530/387

OTHER PUBLICATIONS

Rouslahti, J. Clin. Invest. 87, 1-5 (1991).
Brown & Goodwin, J. Exp. Med. 167, 777-793 (1988).
Gresham et al., J. Cell Biol. 108, 1935-1943 (1989).
Brown et al., J. Cell Biol. 111, 2785-2794 (1990).
Senior et al., Faseb J. 5, A1558 (Abst.) 1991.
Phillips et al., Cell 65, 359-362 (1991).
Smith et al., J. Biol. Chem. 265, 12267-12271 (1990).
Kloczewiak et al., Biochemistry 23, 1767-1774 (1984).

*Primary Examiner*—Lester L. Lee
*Assistant Examiner*—Donna Fox
*Attorney, Agent, or Firm*—Scott J. Meyer

[57] ABSTRACT

A novel hexapeptide is disclosed which has ligand binding specificity of the leukocyte response integrin expressed by human neutrophils and that has the following amino acid sequence Lys Gly Ala Gly Asp Val. [SEQ ID NO: 1]

1 Claim, 8 Drawing Sheets

HEXAPEPTIDE LYS GLY ALA GLY ASP VAL

This invention was made with Government support under Grant No. AI24674 awarded by the National Institutes of Health. The Government has certain rights in the invention.

BACKGROUND OF THE INVENTION

The present invention relates to a novel synthetic hexapeptide which has ligand binding specificity of the Leukocyte Response Integrin (LRI) expressed by human neutrophils.

Phagocytes express several members of the integrin superfamily of adhesive receptors which mediate cell-matrix and cell-cell adhesion (for review see Reference no. 1, appended hereto). These include members of both the VLA ($\beta_1$) family (2,3) and the well-described Leu-CAM ($\beta_2$) family (1). In addition to these molecules, there exists a novel integrin expressed by human neutrophils (PMN) and monocytes which is referred to as the Leukocyte Response Integrin (LRI) (4-6). Structural and immunologic characteristics of LRI suggest that it is a previously undescribed integrin. However, LRI is most closely related to the $\beta_3$ integrin family (cytoadhesins) (4-6). It possesses immunologic cross-reactivity with the platelet antigen gpIIIa ($\beta_3$) and a monoclonal antibody against $\beta_3$ (mAb 7G2) can abrogate LRI-mediated functions (6). mAb 7G2 inhibits Arg-Gly-Asp (RGD)-stimulated phagocytosis by both PMN and monocytes (6) as well as PMN adhesion and chemotaxis to an RGD-containing peptide derived from the basement membrane protein, entactin (7). In addition, LRI is physically and functionally associated with a separate 50 kd plasma membrane antigen, Integrin-associated Protein (IAP) (6). Like mAb 7G2, monoclonal and polyclonal antibodies against IAP inhibit RGD-stimulated phagocytosis by PMN and monocytes (5,6) and PMN adhesion and chemotaxis to the RGD entactin peptide (7). Thus, it is believed that LRI and IAP, as a complex, constitute a signal transduction unit for the activation of phagocytes by RGD-containing adhesive proteins Several adhesive proteins containing RGD sequences can transduce signals for PMN activation via LRI and IAP. In addition to entactin (7), these include fibrinogen, fibronectin, von Willebrand's factor, vitronectin, and collagen type IV (5). Whereas LRI-IAP may transduce the signals necessary for activation, other adhesive receptors may be involved in ligand binding. For example, domains within fibronectin other than the cell-binding domain appear to be involved in phagocyte adhesion (8), even though the RGD sequence within the cell-binding domains is responsible for the augmentation of phagocytosis by both monocytes (8,9) and PMN (5). In addition, fibrinogen (Fg)-stimulated and IAP, yet Fg also binds to a member of the $\beta_2$ integrin family, $\alpha_m\beta_2$ (CD11b/CD18) (10-12). These facts raise the interesting possibility of integrin receptor cooperation in phagocyte activation.

BRIEF DESCRIPTION OF THE INVENTION

In accordance with the present invention a novel synthetic hexapeptide is provided which has ligand binding specificity of the Leukocyte Response Integrin (LRI) expressed by human neutrophils. This novel hexapeptide has the sequence:

Lys Gly Ala Gly Asp Val (KGAGDV) [SEQ ID NO: 1].

It is known that fibrinogen (Fg) contains two RGD sequences within its $\alpha$ chain and a 15 amino acid peptide in the carboxy terminal region of the $\gamma$ chain, $\gamma$384-411, which contains the amino acid sequence AKQAGDV [SEQ ID NO:2] (13-15). Both of these regions are involved in fibrinogen binding to platelet gpIIb/IIIa ($\alpha_{IIb}\beta_3$) (13-15). It has been postulated that several domains of Fg may be involved in ligand binding to PMN, such as the $\gamma$ chain peptide or the region recognized by $\alpha_m\beta_2$ (10), but the RGD sequence would be specific for LRI activation. In accordance with the work described herein, it was found that in fact both RGD and $\gamma$ chain peptides are ligands for LRI. Moreover, when the native $\gamma$ chain sequence, KQAGDV, [SEQ ID NO:3], was mutated to the novel peptide of the present invention, KGAGDV [SEQ ID NO:1], LRI ligand binding and PMN activation were retained. This sequence is not known to be a ligand for any other integrin receptor, including $\alpha_{IIb}\beta_3$, the only previously described receptor for the native Fg $\gamma$ chain peptide. Interestingly, when PMN were stimulated with either FMLP [N-formyl-methyl-leucyl-phenylalanine] or immune complexes, LRI ligand binding specificity was markedly increased for the amino acid sequence KGAGDV and reduced for RGD. That is, when the native sequence, KQAGDV, was mutated by a single amino acid substitution of arginine for alanine to form the peptide KQRGDV [SEQ ID NO:5], it was found that this mutation reduced the potency of the peptide for inhibition of Fg-stimulated ingestion greater than 30 fold. In contrast, the single substitution of a glycine for a glutamine to create the novel peptide of the present invention, KGAGDV, surprisingly and unexpectedly increased the potency of the peptide 4 fold. Antibodies to the $\beta_1$ and $\beta_2$ integrin families had no effect on KGAGDV binding to LRI; whereas antibodies to both $\beta_3$ and IAP inhibited KGAGDV binding to LRI. These data indicate that LRI expresses peptide ligand recognition capabilities which may be regulated by the activation state of the cell. Moreover, the unique amino acid sequence KGAGDV represents a specific ligand for LRI.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in conjunction with the accompanying drawings in which:

FIG. 2 is a graphical representation which shows the effect of mAb's A1A5 (anti-$\beta_1$) and 7G2 (anti-$\beta_3$) on (FIG. 2A) laminin-stimulated ingestion and on (FIG. 2B) fibrinogen-stimulated ingestion. PMN ($1.0 \times 10^5$) were incubated with 0.25 µg of either A1A5, 7G2, or anti-control antibody B3F12 in the presence of 5,000 units of catalase for 15 min at room temperature. Without washing, the mixtures were incubated with EIgG in the presence of buffer or the indicated concentrations of laminin (FIG. 2A) or fibrinogen (FIG. 2B) in a final volume of 115 µl. After 30 min at 37°, ingestion was assessed. PI=number of EIgG ingested by 100 PMN. Data are representative of 3 tests. Anti-$\beta_1$ completely abrogated laminin-stimulated ingestion whereas anti-$\beta_3$ had no effect. In contrast, anti-$\beta_3$ completely abrogated fibrinogen-stimulated ingestion whereas anti-$\beta_1$ shifted dose-response curve for fibrinogen to the right.

FIG. 3 is a graphical representation which shows the effect of peptides containing the aa sequences KQAGDV, KQRGDV, and KGAGDV on fibrinogen-stimulated ingestion. PMN ($1.0 \times 10^5$) were incubated with increasing concentrations of one of the three hexapeptides (KQAGDV, KQRGDV, or KGAGDV) (FIG. 3A) or with either the 15 aa KQAGDV peptide or the 12 aa KGAGDV peptide (FIG. 3B) in the presence of 5,000 units of catalase for 15 min at room temperature. Without washing, the mixtures were incubated with EIgG in the presence of 10 µg/ml of fibrinogen. After 30 min at 37° C., ingestion was assessed. PI=number of EIgG ingested by 100 PMN. Data are repressansative of 2 tests. Data are presented as the % of Fg-stimulated PI (PI=258) plotted against the log of the peptide concentration. The $ID_{50}$'s of the peptides were 2.5 µM (KGAGDV), 10 µM (KQAGDV), 316 µM (KQRGDV), 3.5 µM (15 aa KQAGDV), and 1.1 µM (12 aa KGAGDV). The control peptide KGALEVA [SEQ ID NO:6] at a concentration of 700 µM did not affect Fg-stimulated ingestion. The percent Fg-stimulated PI for 700 µM KGALEVA was 120%. Peptides containing the sequence of KGAGDV were the most potent for inhibition of fibrinogen-stimulated ingestion.

FIG. 5 is a graphical representation which shows the effect of mAb A1A5 (anti-$\beta_1$) on EIgG ingestion stimulated by multivalent, branched RGD peptides (FIG. 5A) or by multivalent, branched KGAGDV peptides (FIG. 5B). PMN ($1.0 \times 10^5$) were incubated with 0.25 µg of either control antibody (3F12) or A1A5 in the presence of 5,000 units of catalase for 15 min at room temperature. Without washing, the mixtures were incubated with EIgG in the presence of either buffer or the indicated concentrations of branched peptides, br-RGD (FIG. 5A) or br-KGAGDV (FIG. 5B). After 30 min at 37° C. ingestion was assessed. PI=number of EIgG ingested by 100 PMN. Data are representative of 2 tests. Anti-$\beta_1$ shifted the dose-response curve for br-RGD to the right in a fashion similar to its effect on fibrinogen-stimulated ingestion (FIG. 2). In contrast, anti-$\beta_1$ had no effect on br-KGAGDV-stimulated ingestion. Anti-$\beta_3$(7G2) inhibited ingestion by both branched peptides.

FIG. 7 is a graphical representation which shows the effect of mAb's IB4 (anti-$\beta_3$), and OKM10 (anti-$\alpha_m$) on multivalent KGAGDV peptide-coated bead binding (FIG. 7A) and multivalent KGAGDV peptide-stimulated ingestion of EIgG (FIG. 7B). FIG. 7A: —PMN ($3.0 \times 10^5$) were incubated with either buffer or the indicated concentrations of mAb's in the presence of 15,000 units of catalase for 15 min at room temperature. Without washing, the mixtures were incubated with br-KGAGDV-coated latex beads in the presence of 1 µM FMLP for 1 hr at 37° C. AI=number of beads bound by 100 PMN. FIG. 7B: —PMN ($1.0 \times 10^5$) were incubated with either buffer or the indicated concentrations of mAb's in the presence of 5,000 units of catalase for 15 min at room temperature. Without washing, the mixtures were incubated with EIgG in the presence of 5 µg/ml of br-KGAGDV. After 30 min at 37° C., ingestion was assessed. PI=number of EIgG ingested by 100 PMN. The diamond symbol represents the level of EIgG ingestion by unstimulated PMN. At a concentration of 0.5 µg antibody/$1.0 \times 10^5$ PMN, only mAb 7G2 significantly inhibited br-KGAGDV-coated bead binding; whereas at the same concentration all three antibodies inhibited br-KGAGDV-stimulated ingestion of EIgG.

FIG. 8 is a graphical representation which shows the effect of the hexapeptides KGAGDV and KQRGDV on multivalent KGAGDV peptide-coated bead binding by control (FIG. 8A) and FMLP-stimulated PMN (FIG. 8B). PMN ($3.0 \times 10^5$) were incubated with either buffer or increasing concentrations of the peptides in the presence of 15,000 units of catalase for 15 min at room temperature. Without washing, the mixtures were incubated with br-KGAGDV-coated latex beads in the presence of 1 μM FMLP (FIG. 8B) or vehicle control (FIG. 8A) for 1 hr at 37° C. AI=number of beads bound by 100 PMN. Data are representative of 2 tests. AI for HSA-coated bead binding to control PMN was 6 and to FMLP-stimulated PMN was 28. The data are presented as the % control br-KGAGDV bead binding [AI=162 for (A) and AI=444 for (B)] plotted against the log of the peptide concentration. The $ID_{50}$'s of both peptides for inhibition of br-KGAGDV-coated bead binding to control PMN were approximately 19 μM. In contrast, the $ID_{50}$ of KQRGDV for inhibition of br-KGAGDV-coated bead binding to FMLP-stimulated PMN was 60 μM whereas the $ID_{50}$ of KGAGDV for inhibition of bead binding to stimulated PMN was approximately 2.5 μM. The control peptide KGALEVA did not affect br-KGAGDV-bead binding to either control or stimulated PMN even at a concentration of 700 μM. The percent control bead binding for 700 μM KGALEVA was 108% for control PMN and 113% for FMLP-stimulated PMN.

References parenthetically cited herein are listed hereinbelow.

Abbreviations used herein are: AI, attachment index; br-KGAGDV, a multivalent, branched peptide containing the aa sequence KGAGDV; EIgG, sheep erythrocyte opsonized with IgG; Fg, fibrinogen; FMLP, N-formyl-methionyl-leucyl-phenylalanine; IAP, integrin associated protein; LAD, leukocyte adhesion deficiency; LRI, leukocyte response integrin; PI, phagocytic index; PMN, polymorphonuclear leukocyte; and RGD, Arg-Gly-Asp.

The novel peptide of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g. the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149-54 (1963) and *Science* 150, 178-85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology*, 32, pp. 221—296, F. F. Nold, Ed., Interscience Publishers, New York, 1969; and Erickson and Merrifield, *The Proteins*, 1 Vol. 2, p. 255 et seq. (ed. Neurath and Hill), Academic Press, New York, 1976.

In order to further illustrate the invention, the following exemplary laboratory preparative work was carried out. However, it will be appreciated that the invention is not limited to these examples or the details described therein.

EXAMPLES

Materials and Methods

Reagents and peptides—N-formyl-methionyl-leucyl-phenylalanine (FMLP) and catalase (bovine liver, 52,000 U/mg) were purchased from Sigma Chemical Co., St. Louis, Mo. FMLP (22.9 mM) was prepared as a stock solution in $Me_2SO$ (Aldrich), stored at $-70°$ C., and diluted into aqueous medium immediately before use. Equivalent concentrations of vehicle were used to control for solvent effects. Chicken egg albumin (ovalbumin) was purchased from Calbiochem-Behring Corp., La Jolla, Calif. Pyrogen-free human serum albumin (HSA) was obtained as a 25% sterile solution from the American Red Cross Blood Services, Washington, D.C. A 10-fold concentrated stock of Hank's balanced salt solution (HBSS) was purchased from Gibco Laboratories, Grand Island, N.Y. Pyrogen-free water for buffer preparation was obtained from Kendall McGaw, Irvine, Calif. Purified human fibrinogen (Fg) was purchased from American Diagnostica Inc., Greenwich, Conn. Purified murine laminin from the EHS sarcoma cell line was the gift of Dr. Hynda Kleinmann, National Institute of Dental Research, Bethesda, Md. Purified rabbit IgG anti-bovine serum albumin (BSA) and purified BSA were purchased from Organon Teknika Corp., West Chester, Pa. The following peptides were obtained as indicated: a 15 aa Fg gamma chain peptide, GQQHHLGGAKQAGDV [SEQ ID NO:7], was purchased from Bachem Inc., Torrence, Calif.; the hexapeptides, GRGDSC, KQAGDV, KGAGDV, KQRGDV, 12 aa Fg gamma chain peptides mutated to HHLGGAKGAGDV [SEQ ID NO:8] and HHLGGAKQRGDV [SEQ ID NO:9], and a control peptide KGALEVA, were prepared by automated solid phase synthesis; the multivalent peptides, branched GRGDSPA (br-RGD), branched KGAGDVA (br-KGAGDV), branched KQAGDVA (br-KQAGDV), and branched KGAGDVA, with a penultimate carboxy terminal Y, (br-Y-KGAGDV) were prepared using 9-fluorenylmethyloxycarbonyl (fmoc) chemistry and the RAMPS system (Dupont Corp., Wilmington, Del.) as based on the synthetic concept of Posnett et al (17). All peptides were purified by HPLC to greater than 80% purity and were analyzed for amino acid composition. In addition, the dodecapeptides, HHLGGAKGAGDV and HHLGGAKQRGDV, were checked further by amino acid sequence analysis. To control for non-specific effects of the peptides on PMN function, the monovalent peptides at concentrations of 500 to 700 μM were checked for inhibition of PDBu-stimulated ingestion of EIgG. The preparation and structure of br-RGD has been previously described (6). The position of the Y in br-Y-KGAGDV allowed radiolabelling with $^{125}$I at a site distant from the receptor binding site.

Antibodies—Purified mAb's were obtained as follows: OKM1 (IgG2b) and OKM10 (IgG2a) (anti-CD11b) were the gifts of Dr. Patricia Rao, the R. W. Johnson Pharmaceutical Research Institute, Raritan, N.J.; IB4 (IgG2a anti-CD18) as previously described (18); A1A5 (IgG1 anti-$\beta_1$) was the gift of Dr. Martin Hemler, Dana Farber Cancer Center, Harvard Medical School, Boston, Mass.; 4B4 (IgG1 anti-$\beta_1$) was purchased from Coulter, Inc., Miami, Fla.; 7G2 (IgG1 anti-$\beta_3$), B6H12 (IgG1 anti-IAP), and F12 (IgG1 anti-$\alpha_v$) were prepared as previously described (5). Polyclonal rabbit IgG anti-IAP antigen was produced and purified as previously described (6). Goat polyclonal IgG anti-VLA 5 was the gift of Dr. Rudolph Juliano, University of North Carolina, Chapel Hill, N.C. Control purified rabbit IgG murine IgG1, murine IgG2a, and murine IgG2b were purchased from Southern Biotechnology Associates, Inc., Birmingham, Ala. The binding of anti-$\beta_1$, anti-$\beta_2$, and anti-$\beta_3$ antibodies to unstimulated and FMLP-stimulated PMN was checked by fluorescent flow microcytometry (5). The mean fluorescence intensitites (MFI) for the test antibodies minus the MFI of the isotype controls were as follows: Anti-$\beta_1$(A1A5) was 41 on unstimulated and 39 on stimulated PMN; anti-$\beta_2$(IB4) was 116 on unstimulated and 145 on stimulated PMN; and anti-$\beta_3$ (7G2) was 42 on unstimulated and 74 on stimulated PMN. The data with anti-$\beta_1$ confirm those of Bohnsack et al (2) which indicated that the expression of $\beta_1$ integrins, unlike the $\beta_2$ integrins, did not increase with PMN stimulation. The data with 7G2 are different from those of Brown and Goodwin (4) which suggested that 7G2 did not recognize PMN. The main reason for this discrepancy is technical; optimal detection of 7G2 reactivity with PMN by flow cytometry requires purified antibody and not tissue culture supernatant and requires stimulation of the PMN. These data confirm the previously published data which indicated that 7G2 inhibited polyvalent RGD-stimulated phagocytosis by PMN (6).

PMN isolation—PMN were isolated as previously described from normal volunteers without hypotonic lysis of the contaminating erythrocytes to prevent possible damage to the PMN (19). Platelet counts were performed on the PMN preparations and were less than 10 platelets/100 PMN. PMN were suspended in HBSS containing 4.2 mM NaHCO$_3$, 10 mM Hepes, 1.5 mM CaCl$_2$, 1.5 mM MgCl$_2$, and 1% ovalbumin, pH 7.4 (HBSS++-1% OVA).

Phagocytosis assay—PMN phagocytosis was assessed by a fluid-phase assay as previously described (5,6). The reaction mixtures are described in the brief description of the figures, hereinbefore. Sheep erythrocytes (E) were purchased from Whittaker M. A. Bioproducts, Walkersville, Md. IgG opsonized E were prepared as previously described (19). Phagocytosis was assessed by light microscopy and quantitated as a phagocytic index (PI), the number of EIgG ingested/100 PMN.

Platelet aggregation assay—Aggregation studies using human platelet rich plasma were performed as previously described (20). Briefly, blood from human volunteers who had not taken any antiplatelet drugs in the previous two weeks was collected into 1/10th volume of CCD buffer (100 mM sodium citrate, 136 mM glucose, pH 6.5). The blood was centrifuged for 3 min at 1000×g and the platelet rich plasma (PRP) was transferred to a plastic tube with a plastic pipet. The PRP was adjusted to 2×10$^8$ platelets/ml with platelet poor plasma (prepared by centrifuging anti-coagulated blood at 2000×g for 15 min) and placed on ice. PRP and control (saline) or test peptides (500 μl) were incubated with 5 μM ADP at 37° C. in a silanized glass cuvette with stirring (900 RPM). The extent of aggregation was monitored with a Payton aggregometer 2 min after the addition of ADP. Inhibition of aggregation for each sample was determined using the following formula: % Inhibition=$(T_{pep}-T_{base})/(T_{agg}-T_{base})\times 100$, where $T_{base}$=% of light transmission in PRP, $T_{agg}$=% of light transmission in the aggregated PRP sample containing the saline control for peptides, and $T_{pep}$=% of light transmission in the aggregated PRP sample containing the peptide inhibitor. Inhibitor potency was expressed as the concentration of inhibitor that resulted in 50% inhibition of aggregation (ID$_{50}$).

Ligand-binding assays—Multivalent ligand binding to LRI was assessed by a fluid-phase assay. Ligand-coated particles were prepared by incubating 1.3 μm aldehyde-modified fluorescent latex beads (Molecular Probes, Eugene, Ore.) at 4.0×10$^8$/ml with 500 μg/ml of either HSA, br-KGAGDV, or the control peptide KGALEVA in HBSS++. After 30 min at 37° C., the beads were centrifuged at 2,000×g for 5 min and resuspended in 1 ml of HBSS++ with 1% HSA and incubated for an additional 30 min at 37° C. to quench any unreacted sites. Approximately 9-11 μg of the coating protein was bound to the beads as assessed by the BCA protein reagent assay (Pierce, Rockford, Ill.). To prevent aggregation, the bead mixture was sonicated for 1-2 sec before addition to the PMN. PMN (3.0×10$^5$) were incubated with either buffer, peptides, or antibodies (as indicated in the brief description of the figures, hereinbefore) in the presence of 15,000 units of catalase for 15 min at room temp. Without washing, the mixtures were incubated with 45 μl of either the HSA-, KGALEVA-, or br-KGAGDV-coated beads in the presence of 1 μM FMLP or vehicle control for 1 hr at 37° C. In addition to FMLP, immune complexes (BSA-anti-BSA) were used to stimulate PMN (21). In some tests, unbound beads were removed from PMN-bound beads by overlayering the mixture on 400 μl of Hypaque-Ficoll and centrifuging. The unbound beads remained at the interface whereas the pellet contained the PMN-bound beads. Attachment was assessed by fluorescence microscopy and quantitated as an attachment index (AI), the number of beads bound by 100 PMN.

Soluble ligand binding was assessed by incubating radiolabelled br-Y-KGAGDV with PMN as previously described for $^{125}$I-cc-RGDS binding to PMN (5). br-Y-KGAGDV (1 mg) was radiolabelled with $^{125}$I by using Iodo-Gen (Pierce, Rockford, Ill.) as the oxidizing agent (5). The specific activity of the labelled peptide was 4.6×10$^5$ CPM/μg. PMN were incubated with labelled peptide (3 μg/5.0×10$^5$ PMN) in the presence of catalase in a 1.5 ml Eppendorf tube for 30 min at 37° C. The mixtures were overlayered on Versilube (General Electric Co., Wilmington, Mass.) and centrifuged at 12,000×g to assess pellet-associated radioactivity. Specific binding was determined by subtracting the radioactivity bound in the presence of 100-200 μg of unlabelled br-Y-KGAGDV from total binding.

Results

Figure 1:
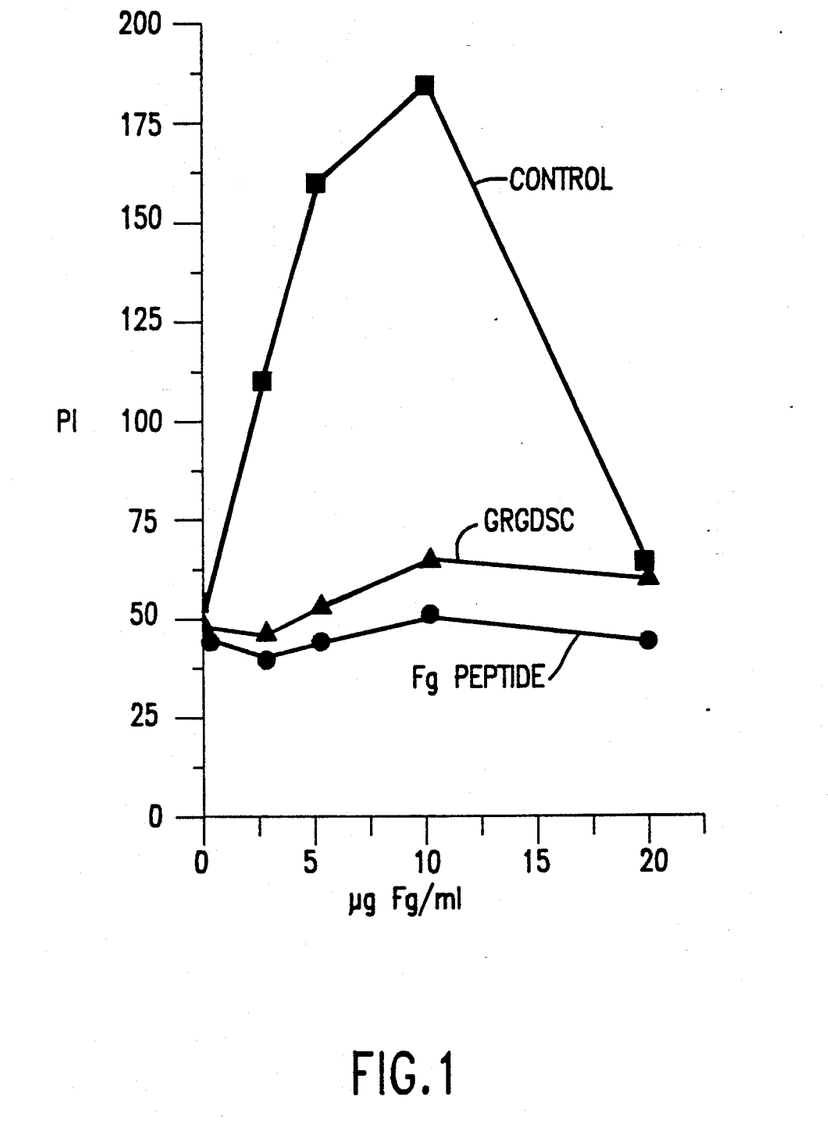
FIG. 1 is a graphical representation which shows the effect of the fibrinogen gamma chain peptide and GRGDSC [SEQ ID NO:4] on fibrinogen-stimulated ingestion of EIgG by PMN. PMN ($1.0 \times 10^5$) were incubated with 25 $\mu$g of either a control peptide (peptide 32, GHGPGEQQLR [SEQ ID NO:11]), GRGDSC, or a 15 aa Fg $\gamma$ chain peptide in the presence of 5,000 units of catalase for 15 min at room temperature. Without washing, the mixtures were incubated with EIgG in the presence of buffer or the indicated concentration of fibrinogen in a volume of 115 $\mu$l. After 30 min at 37° C., ingestion was quantitated as a phagocytic index. PI=- number of EIgG ingested by 100 PMN. Data are representative of 3 tests. Both GRGDSC and the 15 aa Fg γ chain peptide were capable of abrogating fibrinogen-stimulated ingestion, whereas neither had an effect of the level of ingestion by unstimulated PMN.
Figure 2A:
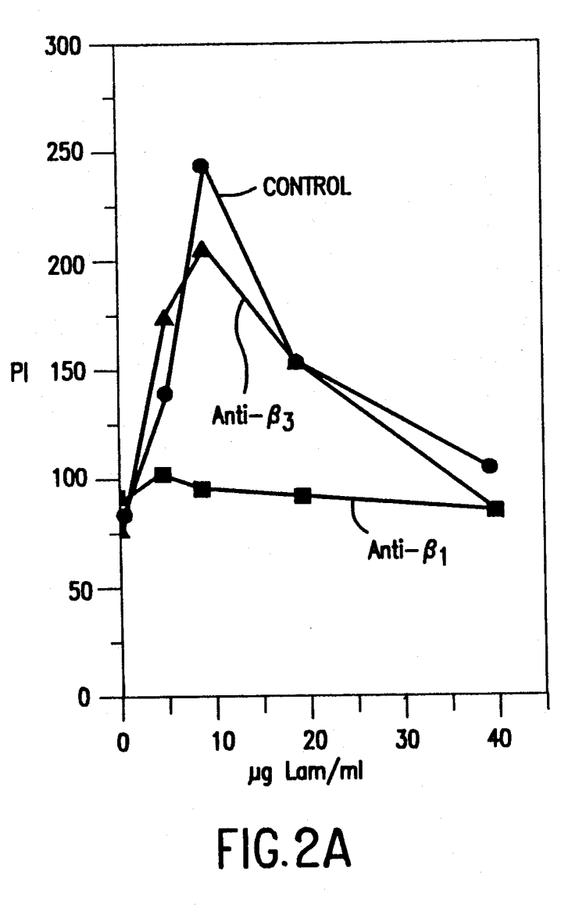
Figure 2B:
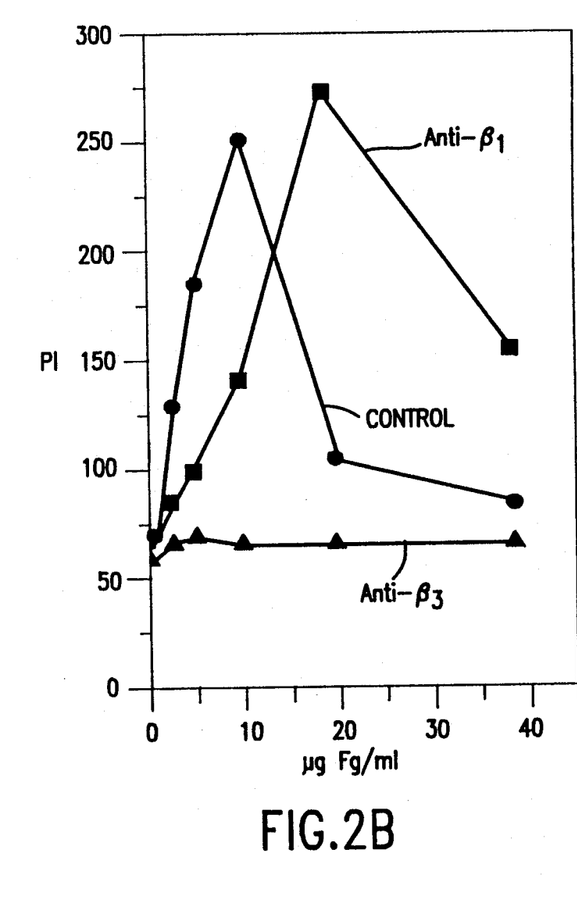

Both RGD-containing and Fg γ chain peptides abrogate Fg-stimulated ingestion mediated by LRI—To begin investigation of the ligand binding specificity of LRI, it was asked if Fg-stimulated ingestion could be affected by peptides containing the γ chain aa sequence as well as by peptides containing the RGD sequence. As has been shown previously (5), Fg stimulated EIgG ingestion 3-4 fold in a bi-phasic manner. Incubation of PMN with either GRGDSC or the 15 aa γ chain peptide completely abrogated the ability of Fg to stimulate ingestion of EIgG, whereas neither peptide had any effect on the level of EIgG ingestion by unstimulated PMN (FIG. 1). A control peptide of irrelevant sequence, peptide 32 (5), had no effect on Fg-stimulated ingestion (FIG. 1). These data indicated that two distinct aa sequences within Fg could be involved in augmentation of phagocytosis. One possibility to explain these data was that two distinct receptors were involved, both of which would be essential for signal transduction by Fg for the augmentation of ingestion. Alternatively, as with $\alpha_{IIb}\beta_3$, the two sites could be recognized by the same receptor, LRI. To investigate these alternatives, the effect of mAb's to $\beta_1$ and $\beta_3$ Fg-stimulated ingestion was examined. First, the effect of anti-$\beta_1$ on Fg-stimulated ingestion was examined. Although controversial, $\beta_1$ integrins have been described on PMN (2,3) and anti-$\beta_1$ binding to PMN was confirmed. (see Materials and Methods). To determine that mAb A1A5 (anti-$\beta_1$) could block $\beta_1$-dependent functions by PMN, its effect on laminin-stimulated ingestion of EIgG was examined. PMN interact with laminin via $\alpha_6\beta_1$ (2). As shown in FIG. 2A, anti-$\beta_1$ completely abrogated the ability of laminin to stimulate ingestion. In contrast, anti-$\beta_1$ did not inhibit Fg-stimulated ingestion, though it did shift the dose response curve of Fg to the right (FIG. 2B). Identical data were obtained with another mAb against $\beta_1$ (4B4) and with a polyclonal antibody to $\alpha_5\beta_1$. In contrast, anti-$\beta_3$ (mAb 7G2) completely abrogated Fg-stimulated ingestion (FIG. 2B) without affecting laminin-stimulated ingestion (FIG. 2A). These data indicate that $\beta_1$ integrin(s) are essential for PMN activiation by laminin. In addition, some member(s) of the $\beta_1$ family may be involved in binding Fg; however, all signal transduction for Fg-enhanced ingestion requires mAb 7G2-inhibitable, $\beta_3$-like integrin. These data confirm the previous data which indicated that mAb 7G2 inhibited polyvalent RGD-stimulated ingestion by both monocytes and PMN (6). Because LRI is the only known integrin on PMN recognized by anti-$\beta_3$ reagents (6), LRI is the integrin via which Fg stimulated PMN phagocytic function. This suggests the hypothesis that LRI is able to recognize both RGD and Fg γ chain sequences.

Figure 3A:
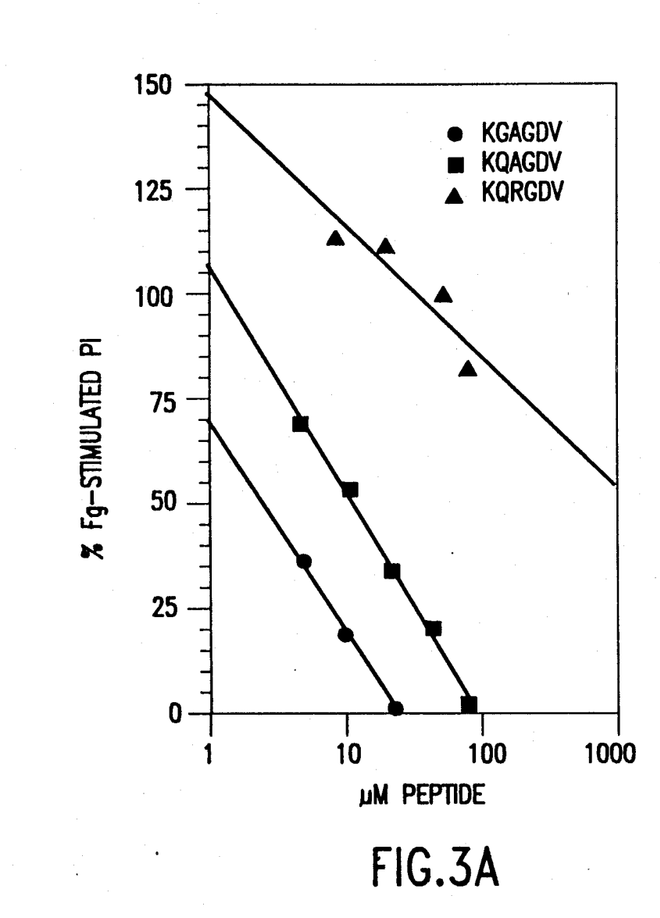
Figure 3B:
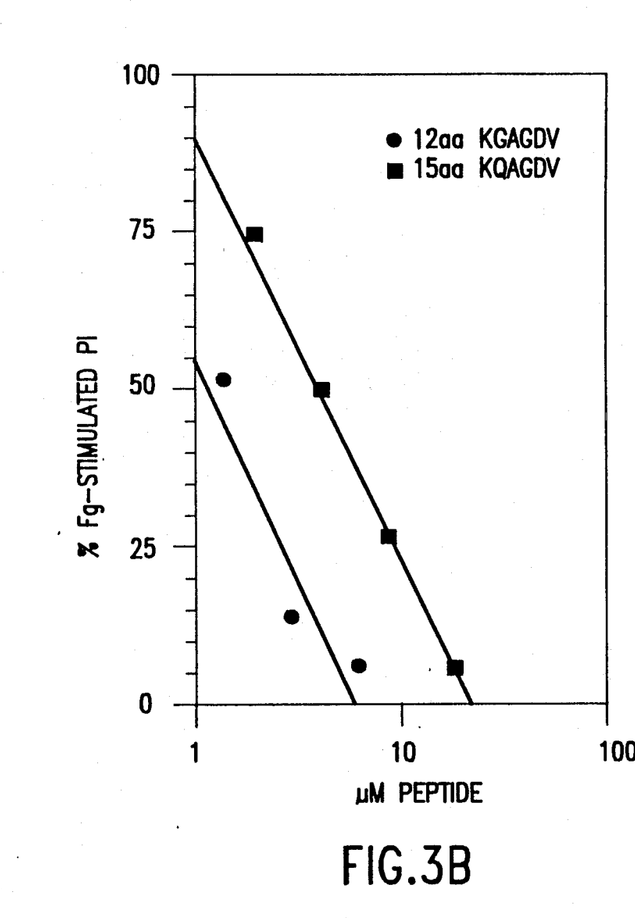

Peptides containing the sequence KGAGDV are more specific for inhibiton of LRI-mediated phagocytosis enhancement than are RGD-peptides—To begin to investigate the amino acids important in γ chain recognition by LRI, PMN were incubated with increasing concentrations of three separate hexapeptides, KQAGDV, KQRGDV, and KGAGDV, to assess their effect on Fg-stimulated ingestion of EIgG. KQAGDV represents the 6 most carboxy terminal amino acids in the 15 aa γ chain peptide and is necessary for $\alpha_{IIb}\beta_3$ recognition of the γ chain (15). This peptide inhibited Fg-stimulated ingestion with an approximate ID$_{50}$ of 10 $\mu$M (FIG. 3A). Because LRI is known to recognize the sequence RGD, the peptide KQRGDV, containing the single aa substitution of an arginine for an alanine, was investigated. Surprisingly, this mutation reduced the potency of the peptide for inhibition of Fg-stimulated ingestion greater than 30 fold (FIG. 3A). In contrast, the single substitution of a glycine for a glutamine, creating the novel peptide of the present invention KGAGDV, increased the potency of the peptide by 4 fold. This hexapeptide, KGAGDV, inhibited Fg-stimulated ingestion with an ID$_{50}$ of approximately 2.5 $\mu$M (FIG. 3A). The control peptide KGALEVA, even at a concentration of 700 $\mu$M, had no effect on Fg-stimulated ingestion. The percent Fg-stimulated PI for 700 $\mu$M KGALEVA was 120%. Because increasing the length of the γ chain peptide to include the two histidines just amino terminal to KQAGDV increases the potency of the γ chain peptide for inhibition of Fg-stimulated platelet aggregation (15), it was asked if the KGAGDV sequence would also be more potent for inhibition of LRI-stimulated ingestion if the histidines were present. Therefore, the ability of the 15 aa KQAGDV peptide was compared with a 12 aa KGAGDV peptide (both of which contain both histidines) to inhibit Fg-stimulated ingestion. As shown in FIG. 3B, even with the additional histidine residues, the peptide containing the sequence KGAGDV was 3 fold more potent at inhibiting Fg-stimuated ingestion than was the 15 aa KQAGDV peptide. The 12 aa KGAGDV peptide inhibited Fg-stimulated ingestion with an ID$_{50}$ of approximately 1.2 $\mu$M. Both peptides were 2-3 fold more potent than their hexameric cores. These data demonstrate that the hexapeptide sequence KGAGDV is a potent inhibitor of Fg-activation of PMN. Because Fg stimulates phagocytosis through LRI, these data suggest that KGAGDV is a peptide ligand for LRI.

Because LRI appears to be closely related to the $\beta_3$ integrins, it was important to ascertain the activity of KGAGDV-containing sequences against a prototype $\beta_3$ integrin. $\alpha_{IIB}\beta_3$ was chosen for these studies. To accomplish this aim, HHLGGAKQAGDV, HHLGGAKQRGDV, and HHLGGAKGAGDV were examined for their ability to inhibit ADP-stimulated aggregation of human platelet rich plasma, an $\alpha_{IIb}\beta_3$-dependent function which is also dependent on Fg. As depicted in Table I, these FG γ chain-derived peptides were compared for their ability to inhibit Fg-stimulated platelet aggregation and Fg-stimulated ingestion by PMN. In correspondence with published values (22), the native dodecapeptide sequence inhibited platelet aggregation with an ID$_{50}$ of 80 $\mu$M. The arginine substituted peptide was an even more potent inhibitor of platelet aggregation (ID$_{50}$=28 $\mu$M), whereas it had little inhibitory effect on Fg-stimulated ingestion (0% inhibition at 80 $\mu$M). In striking contrast, the glycine substituted peptide was completely ineffective as an inhibitor of platelet aggregation (0% inhibition at 100 $\mu$M), whereas it was a potent inhibitor of Fg-stimulated ingestion (ID$_{50}$=1.1 $\mu$M). These data suggest that the gly-substituted peptide (HHLGGAKGAGDV) binds $\alpha_{IIb}\beta_3$ very poorly, if at all, and that LRI and $\alpha_{IIb}\beta_3$ express different peptide ligand-binding specificities.

Figure 4:
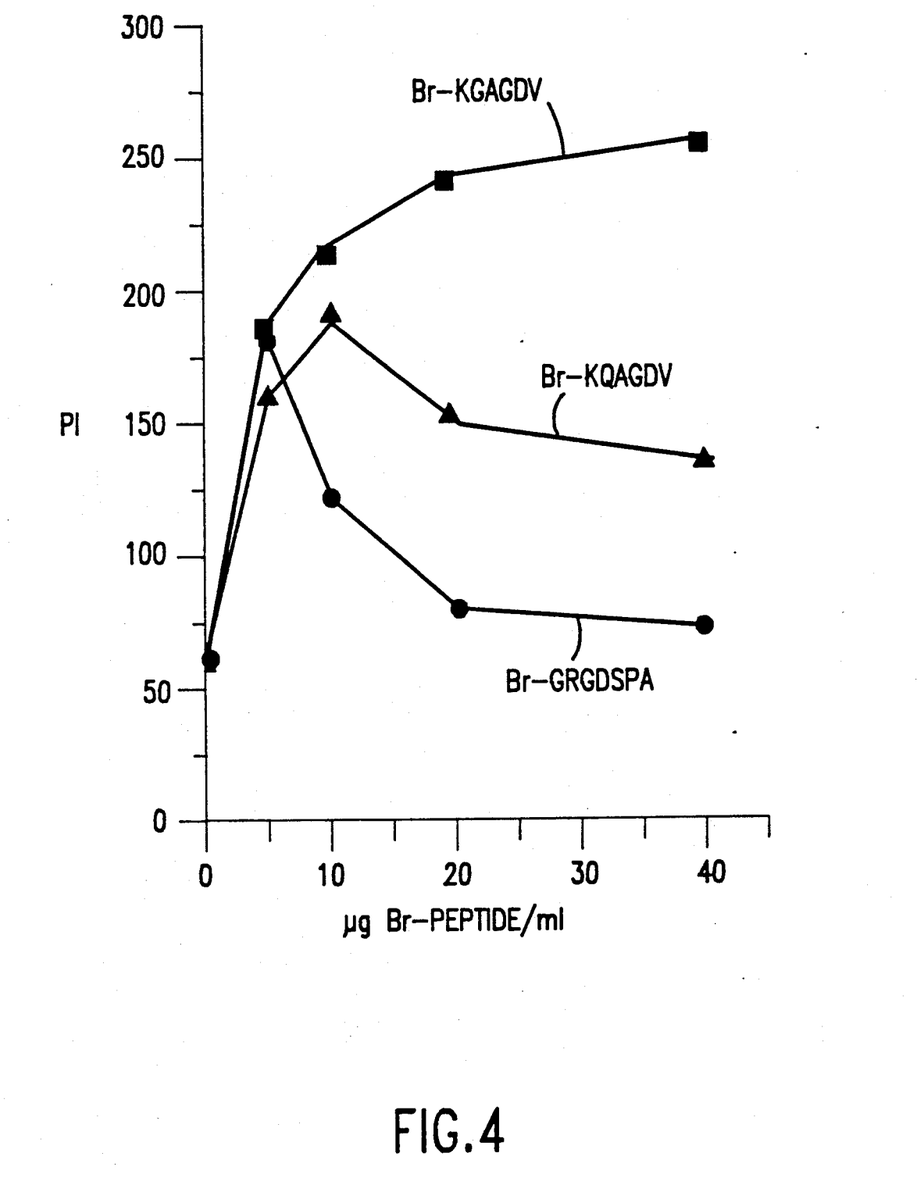
FIG. 4 is a graphical representation which shows the effect of multivalent peptides containing aa sequences RGD, KQAGDV, and KGAGDV on the ingestion of EIgG by PMN. PMN ($1.0 \times 10^5$) and EIgG were incubated with either buffer or the indicated concentrations of multivalent, branched peptides (br-RGD, br-KQAGDV, or br-KGAGDV) in the presence of 5,000 units of catalsae. After 30 min at 37° C. ingestion was assessed. PI=number of EIgG ingested by 100 PMN. Data are representative of 3 tests. Multivalent peptides containing the aa sequence KGAGDV were more potent at stimulating ingestion and exhibited a wider dose-response range than multivalent peptides containing the sequence RGD.
Figure 5A:
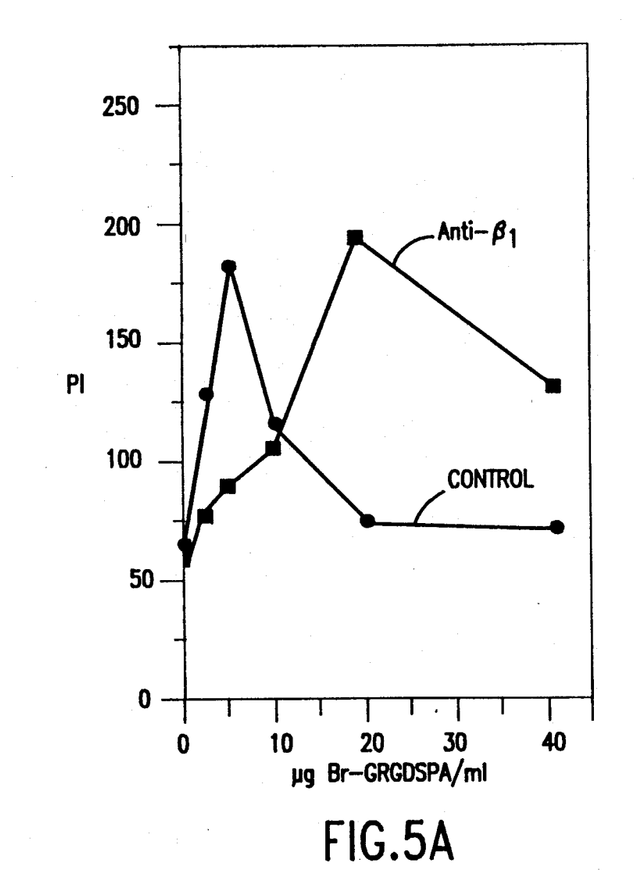

To determine whether the Fg γ chain-derived peptide inhibitors could also act as agonists for LRI, a set of multivalent, branched peptides containing the sequences of RGD, KQAGDV, and KGAGDV was constructed. It has been shown previously that multivalent peptides are necessary to stimulate PMN ingestion of EIgG via LRI (5,6). As shown in FIG. 4, all three branched peptides stimulated ingestion of EIgG. However, br-KGAGDV was the most potent and effacious over the dose-response range examined. Br-RGD and br-KQAGDV exhibited the same relative potency for stimulation of ingestion that they exhibited as monovalent peptides for inhibition of Fg-stimulated ingestion (compare FIG. 4 with FIG. 3A). Because anti-$\beta_1$ shifted the dose-response curve for Fg-stimulated ingestion to the right, the effect of anti-$\beta_1$ on the ability of br-RGD and br-KGAGDV to stimulate ingestion of EIgG was examined. As with Fg, anti-$\beta_1$ shifted the dose-response curve of the br-RGD peptide to the right (FIG. 5A). In contrast, anti-$\beta_1$ had no effect on the dose-response curve of br-KGAGDV. Anti-LRI (mAb 7G2) completely inhibited the ability of all three branched peptides to stimulate ingestion. These data indicate that multivalent RGD peptides bind to at least two distinct families of integrins on PMN. Multivalent KGAGDV, however, appears to be functionally specific for LRI. The order of functional potency of these peptides for LRI is KGAGDV>KQAGDV>KQRGDV=GRGDSPA [SEQ ID NO:10].

Figure 6:
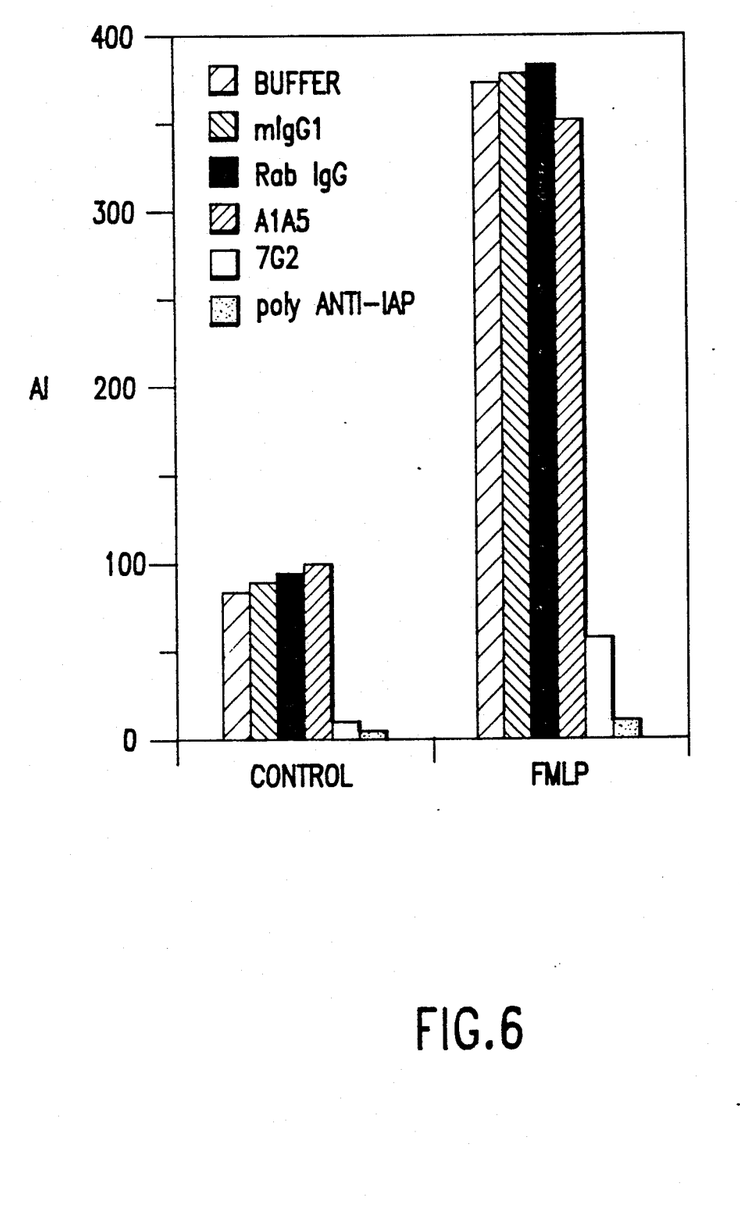
FIG. 6 is a bar graph which shows the effect of A1A5 (anti-$\beta_1$), 7G2 (anti-$\beta_3$), and polyclonal anti-IAP on the ability of unstimulated and FMLP-stimulated PMN to bind latex beads coated with multivalent branched KGAGDV peptides. PMN ($3.0 \times 10^5$) were incubated with either buffer, 2 µg murine IgG1, 6 µg rabbit IgG, 2 µg A1A5, 2 µg 7G2, or 6 µg polyclonal anti-B6H12 in the presence of 15,000 units of catalase for 15 min at room temperature. Witho​ut washing, the mixtures were incubated with either HSA-, KGALEVA-, or br-KGAGDV-coated 1,3 µm aldehyde-modified latex beads in the presence of 1 µM FMLP or vehicle control. After 1 hr at 37° C., adhesion was assessed as an attachment index. AI=number of beads bound by 100 PMN. AI's for HSA-coated beads were 5 for control cells and 58 for FMLP-stimulated PMN. AI's for KGALEVA-coated beads were 12 for control cell and 65 for FMLP-stimulated PMN. The AI's for br-KGAGDV-coated bead binding to FMLP-stimulated PMN varied with a range of AI's from 148–468. The mean AI for br-KGAGDV-bead binding to FMLP-stimulated PMN was 317±47 SEM, n=7. Neither anti-$\beta_1$ nor any of the control antibodies had any effect on br-KGAGDV-coated bead binding to either control or FMLP-stimulated PMN. In contrast, both antibodies which inhibit LRI function, 7G2 and anti-IAP, inhibited br-KGAGDV-coated bead binding.

Multivalent, branched KGAGDV binds specifically to LRI and not to $\beta_1$ or $\beta_2$ integrins—In order to prove that br-KGAGDV represented a specific ligand for LRI, two ligand binding assays were employed. First, the binding of br-KGAGDV-coated, KGALEVA-coated, and HSA-coated latex beads to PMN was examined and the ability of anti-LRI(7G2) and anti-IAP (polyclonal) to inhibit binding was tested. The binding of br-KGAGDV-beads to unstimulated PMN was modest but significant and was enhanced significantly by stimulation of the PMN with either FMLP (FIG. 6) or immune complexes (21). The mean AI for br-KGAGDV-bead binding to FMLP-stimulated PMN was 317±47 SEM, n=7. This binding was specific because it could be inhibited by the inclusion of excess KGAGDV (FIG. 8). Binding of HSA-coated beads to either control or stimulated PMN was minimal. The AI's for HSA-bead binding to control and FMLP-stimulated PMN were 5 and 58, respectively. The AI's for the control peptide KGALEVA-coated bead binding were 12 and 65, respectively for control and FMLP-stimulated PMN, values not significantly different from those for HSA-bead binding. Whether the PMN were stimulated with FMLP or not, both anti-LRI and anti-IAP, but not isotype control antibodies, significantly inhibited br-KGAGDV-bead binding (FIG. 6). When antibody inhibition studies from three tests were compared, anti-LRI inhibited br-KGAGDV-bead binding to FMLP-stimulated PMN by 79% (p<0.02) and anti-IAP inhibited by 94% (p<0.006, by t-test). In addition, when anti-IAP was added after 45 min at 37° C., 75% of the PMN-bound beads were removed, indicating that br-KGAGDV-beads were primarily plasma membrane-bound and not ingested. These data suggest that br-KGAGDV-beads bind to PMN in an LRI- and IAP-dependent manner. Second, the binding of radiolabelled br-Y-KGAGDV to PMN was examined and the ability of anti-LRI and anti-IAP to inhibit binding was tested. PMN bound specifically 37,463±3,436 br-Y-KGAGDV molecules/PMN (Table II). Anti-LRI (7G2) reduced the number of specific molecules bound/PMN to 7,212±5,662 (p<0.01) with inhibition of 80.8% In addition anti-IAP (mAb B6H12) reduced the number/PMN to 1,098±762 (p<0.001, t-test) with a mean inhibition of 97.1%. Isotype control antibodies did not affect the binding of specific radiolabelled ligand to LRI. These data indicate that multivalent, branched KGAGDV peptides bind specifically to LRI expressed by both unstimulated and stimulated PMN.

Figure 7A:
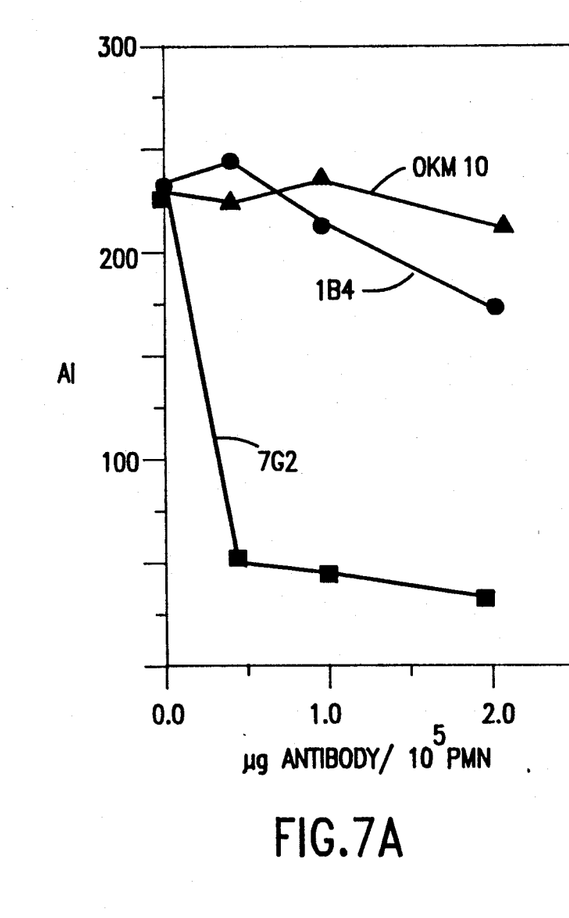
Figure 7B:
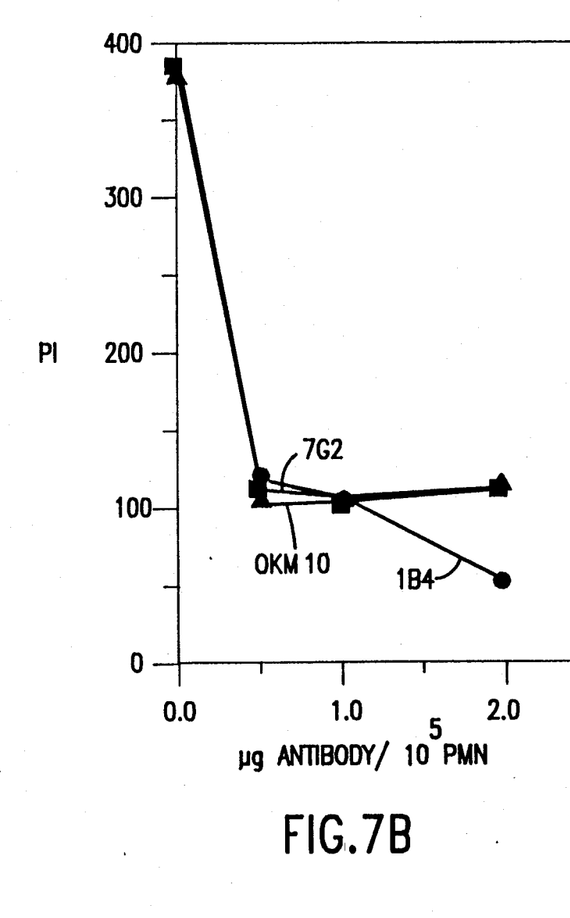

To investigate the contribution of the $\beta_1$ and $\beta_2$ integrins to br-KGAGDV binding, the ability of anti-$\beta_1$(mAbA1A5), anti-$\beta_2$ (IB4) and anti-$\alpha_m$ (OKM1 and OKM10) to inhibit br-KGAGDV-bead binding to FMLP-stimulated PMN was investigated. As shown in FIG. 6, anti-$\beta_1$ had no effect on br-KGAGDV-bead binding to stimulated PMN. In addition, incubation of PMN with 0.5 μg of either mAb IB4 or the same isotype mAb OKM10 had no effect on br-KGAGDV-bead binding (FIG. 7A), mAb OKM1 gave identical results. In contrast, this same concentration of mAb 7G2 (anti-LRI) completely inhibited br-KGAGDV-bead binding down to the level observed for HSA-beads. Interestingly, the same concentration of anti-$\alpha_m\beta_2$ antibodies, which did not inhibit br-KGAGDV-bead binding, completely abrogated the ability of br-KGAGDV to stimulate ingestion of EIgG (FIG. 7B). These data are consistent with the previous observation that $\alpha_m\beta_2$ plays a non-ligand binding role in phagocytosis stimulated by multiple PMN activators, including phorbol esters (18, 21). At higher concentrations of antibody, the effect of mAbs 7G2 and OKM10 remained the same, whereas mAb IB4 resulted in a 24% inhibition of br-KGAGDV-bead binding (FIG. 7A). At this same concentration of mAb IB4, ingestion of EIgG by unstimulated PMN also was inhibited partially (FIG. 7B). These data are consistent with the previous work which has shown that ingestion by unstimulated PMN does not require the $\beta_2$ integrins but that some antibodies which recognize $\alpha_m$ (Mol) or $\beta_2$ (IB4) can inhibit this ingestion non-specifically (21). Therefore, these data indicate that neither the $\beta_1$ nor the $\beta_2$ integrins play a significant role in binding br-KGAGDV-coated beads.

Figure 8A:
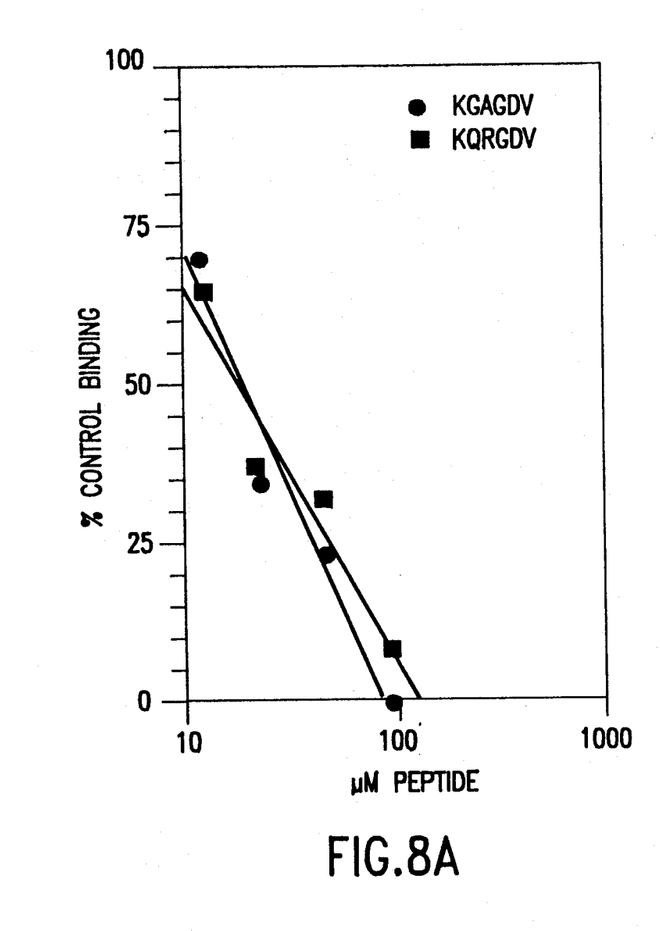
Figure 8B:
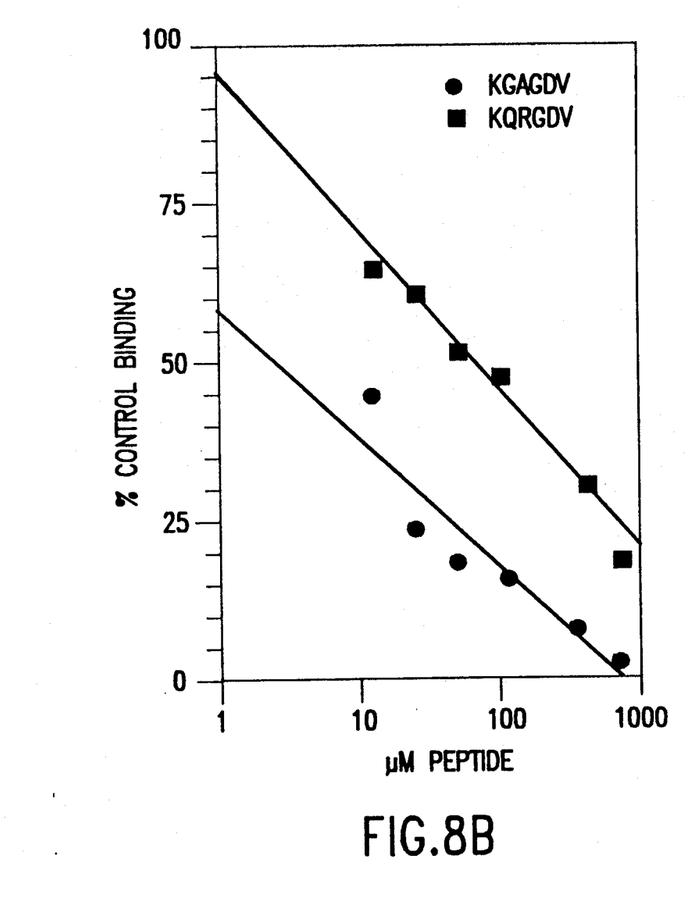

Stimulation of PMN regulates LRI ligand binding specificity—Because the present data indicated that both RGD and KGAGDV aa sequences could be functionally recognized by LRI and that binding of br-KGAGDV-beads to unstimulated PMN was via LRI, the ability of the hexapeptides KGAGDV and KQRGDV, and the control peptide KGALEVA, to inhibit br-KGAGDV-bead binding was investigated. Both hexapeptides were equally potent at inhibiting br-KGAGDV-bead binding to unstimulated PMN with and ID$_{50}$ of 19 μM (FIG. 8A). In marked contrast, the hexapeptides differed in their ability to inhibit br-KGAGDV-bead binding to FMLP-stimulated PMN (FIG. 8B). With stimulation, the potency of KQRGDV for inhibition was reduced approximately 3 fold with a resultant ID$_{50}$ of 60 μM. Interestingly, the potency of monovalent KGAGDV for inhibition was increased approximately 8 fold by PMN stimulation with a resultant ID$_{50}$ of 2.5 μM (FIG. 8B). In fact, this concentration of KGAGDV was identical to that required to inhibit Fg-stimulated ingestion by 50% (2.5 μM, FIG. 3A). Therefore, the ability of KGAGDV to inhibit ligand binding and to inhibit a function stimulated upon ligand binding was identical. Even at a concentration of 700 μM, the control peptide KGALEVA, did not affect br-KGAGDV-bead binding to either unstimulated or FMLP-stimulated PMN. The percent control bead binding for 700 μM KGALEVA was 108% for unstimulated PMN and 113% for FMLP-stimulated PMN. These data indicate that the activation state of the PMN regulates the ligand binding specificity of LRI. Thus, with PMN stimulation, as would occur in the presence of IgG-opsonized targets or chamotactic peptides, there is a significant increase in the ability of LRI to preferentially recognize the sequence KGAGDV as compared to the sequence RGD, whereas in the absence of stimulation, both sequences are recognized equally.

The data herein describe a unique ligand binding specificity for the leukocyte response integrin, LRI. Previous work has indicated that LRI is a novel, previously undescribed integrin which exhibits immunologic cross-reactivity with the β chain of the cytoadhesin family, $\beta_3$ (gp IIIa) (4-6). Like the cloned $\beta_3$ integrins, LRI recognizes the peptide sequence Arg-Gly-Asp (5). It is shown herein that LRI, like $\alpha_{IIb}\beta_3$, recognizes the carboxy terminal peptide of the Fg γ chain. This peptide contains the sequence KQAGDV and has been shown to cross-link to aa 294-314 of $\alpha_{IIb}$ (23). Interestingly, published studies indicate that the other member of the cytoadhesin family, $\alpha_v\beta_3$, does recognize this sequence within Fg (14). In the present disclosure, incubation of PMN with a 15 aa peptide containing the sequence KQAGDV markedly inhibited Fg-stimulated ingestion of EIgG. The ID$_{50}$ for this response was 3.5 μM (FIG. 3B). In comparison, the native γ chain dodecapeptide inhibited $\alpha_{IIb}\beta_3$-dependent platelet aggregation with an ID$_{50}$ of 80 μM (Table I). These data indicate that like $\alpha_{IIb}\beta_3$, LRI recognizes the Fg γ chain peptide. Moreover, unlike any other known integrin, LRI also recognizes the aa sequence KGAGDV. This is shown by inhibition of LRI function by monovalent KGAGDV (FIG. 3, ID$_{50}$=2.5 μM) and by the fact that a multivalent, branched peptide containing this sequence (br-KGAGDV) binds specifically to LRI and can stimulate LRI-dependent augmentation of phagocytosis (Table II, FIG. 5, and FIG. 6). This is in direct contrast to the inability of KGAGDV peptides to inhibit $\alpha_{IIb}\beta_3$-dependent platelet aggregation (Table I). The order of potency of the Fg γ chain-derived peptides for inhibition of LRI-dependent functions is KGAGDV>KQAGDV>KQRGDV, whereas the ability of the dodecapeptides which contain these sequences to inhibit Fg-dependent platelet aggregation exhibits a reverse order of potency (Table I). These data suggest that the novel sequence KGAGDV is preferentially recognized by LRI, further discriminating it from the known cytoadhesin family members.

Figure 5B:
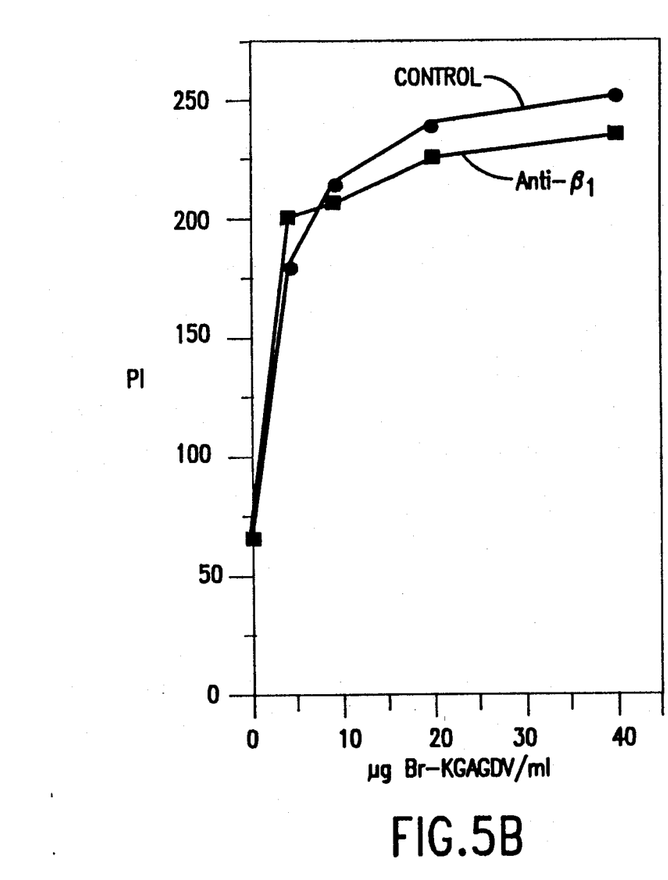

To prove that br-KGAGDV was a specific ligand for LRI and was not recognized by any other integrins expressed by PMN, the ability of several antibodies which recognize integrins to inhibit binding of br-KGAGDV-coated beads to PMN (FIG. 6 and FIG. 7) and br-KGAGDV-stimulated ingestion of EIgG (FIG. 5B and FIG. 7B) were examined. Because at least 2 members of the $\beta_1$ family, $\alpha_5\beta_1$ (3) and $\alpha_6\beta_1$ (2), have been detected on PMN and antibodies against $\beta_1$ can inhibit the function of both of these integrins, the ability of 3 antibodies which recognize $\beta_1$ (2-monoclonal, 1 polyclonal) to inhibit br-KGAGDV-coated bead binding were examined. Whereas these three antibodies altered the dose-response curve for Fg-stimulated ingestion and inhibited lamin-stimulated ingestion (FIG. 2), none had any effect on br-KGAGDV ligand binding (FIG. 6) or on br-KGAGDV-stimulated ingestion (FIG. 5). The leukocyte integrin, $\alpha_m\beta_2$, is known to recognize Fg and antibodies to both the α chain (10) and the β chain (12) can inhibit PMN interactions with Fg. Neither OKM1 nor OKM10 (anti-$\alpha_m$) had any affect on br-KGAGDV-bead binding to FMLP-stimulated PMN (FIG. 7). In contrast, OKM1 has been shown previously to inhibit binding of the 30 kD region of the Fg D peptide to FMLP-stimulated PMN (10). In addition, mAb IB4 (anti-$\beta_2$) has been shown to inhibit the adhesion of cytokine-stimulated PMN to Fg (12), whereas even at the highest concentration tested in the present work, it only inhibited Br-KGAGDV-bead binding by 24% (FIG. 7A). These data are consistent with previous data which indicated that the $\beta_2$ integrins were not necessary for ligand binding by LRI (5). In addition, the ability of PMN from a patient with LAD to bind radiolabelled br-KGAGDV was examined and it was found that the LAD PMN were equally capable as normal PMN for br-KGAGDV-specific binding. Interestingly, even though these anti-$\alpha_m\beta_2$ antibodies did not significantly inhibit ligand binding, all three inhibited ingestion of EIgG stimulated by br-KGAGDV (FIG. 7B). It has been proposed previously that $\alpha_m\beta_2$ plays a non-ligand binding role in phagocytosis stimulated by numerous agents, including extracellular matrix proteins and phorbol esters (18, 19, 21). The present data confirm the hypothesis by further differentiating the ligand-binding functions of $\alpha_m\beta_2$ from its role in phagocytosis.

Previous work indicated that LRI recognized RGD-containing adhesive proteins and that a multivalent peptide cc-RGDS could specifically bind to PMN and stimulate ingestion of EIgG (5). Therefore, it became important, in light of the present data, to understand the relationship of RGD and KGAGDV peptides for ligand recognition by LRI. It was found that unstimulated PMN recognized both sequences equally (FIG. 8A), whereas PMN stimulated with either FMLP or immune complexes preferentially recognized KGAGDV as compared to RGD (FIG. 8B). These data indicate that both RGD and KGAGDV sequences are recognized by LRI and that the activation state of the PMN regulates the ligand-binding specificity of LRI for these two sequences. Thus, LRI, like $\alpha_{IIb}\beta_3$ (1, 13) and the $\beta_2$ integrins (1), demonstrates stimulus-dependent modulation of ligand binding.

TABLE I

Comparison of γ-chain derived peptides for inhibition of Fg-stimulated platelet aggregation and Fg-stimulated ingestion by PMN.

| Peptide | Platelet ID$_{50}$[a] | PMN ID$_{50}$[b] |
|---|---|---|
| GQQHHLGGAKQAGDV | N.D. | 3.5 μM |
| HHLGGAKQAGDV | 80 μM | ~ N.D. |
| HHLGGAKQRGDV | 28 μM | >80 μM[c] |
| HHLGGAKGAGDV | >100 μM[d] | 1.1 μM |

[a]Platelet aggregation was assessed as described in the Materials and Methods.
[b]Fg-stimulated ingestion of EIgG by PMN was assessed as described in the Materials and Methods.
[c]0% inhibition at 80 μM.
[d]0% inhibition at 100 μM.

TABLE II

Binding of Radiolabelled br-Y-KGAGDV to PMN

| | Specific Molecules/PMN[a] | % Inhibition |
|---|---|---|
| BUFFER | 37,463 ± 3,436 | 0 |
| MIgG1 | 34,412 ± 1,879 | 8.1 |
| MIgG2b | 37,219 ± 4,122 | 0.6 |
| 7G2 | 7,212 ± 5,662 | 80.8 |

TABLE II-continued

Binding of Radiolabelled br-Y-KGAGDV to PMN

| | Specific Molecules/PMN[a] | % Inhibition |
|---|---|---|
| B6H12 | 1,098 ± 762 | 97.1 |

[a] PMN (5.0 × 10$^5$) were incubated with buffer or 2.5 μg of purified antibody in the presence of catalase for 15 min at room temp. Radiolabelled br-Y-KGAGDV (3 μg) was added in the presence and absence of 100–200 μg of unlabelled br-Y-KGAGDV to determine cell-associated specific binding as described in Materials and Methods. Data are represented as the mean ± SEM of triplicate samples. Due to day to day variability in binding, data from a single experiment are depicted. The number of specific br-Y-KGAGDV molecules bound/PMN ranged from 16,100 to 37,463 with a mean = 27,475 ± 5,471 SEM, n = 4 from averaged duplicate or triplicate samples. The effects of the antibodies were qualitatively similar for all experiments.

Various other examples will be apparent to the person skilled in the art after reading the present disclosure without departing from the spirit and scope of the invention. It is intended that all such other examples be included within the scope of the appended claims.

REFERENCES

1. Ruoslahti, E. (1991) J. Clin. Invest. 87, 1–5
2. Bohnsack, J., Akiyma, S., Damsky, C., Knape, W., and Zimmerman, G. (1990) J. Exp. Med. 171, 1221–1237
3. Singer, I., Scott, S., Kawka, D., and Kazazis, D. (1989) J. Cell Biol. 109, 3169–3182
4. Brown, E., and Goodwin, J. (1988) J. Exp. Med. 167, 777–793
5. Gresham, H., Goodwin, J., Allen, P., Anderson, D., and Brown, E. (1989) J. Cell Biol. 108, 1935–1943
6. Brown, E., Hooper, L., Ho, T., and Gresham, H. (1990) J. Cell Biol. 111, 2785–2794
7. Senior, R., Griffin, G., Gresham, H., and Chung, A. (1991) FASEB Journal 5, A1558 (Abstr.)
8. Bohnsack, J., Takahashi, T., and Brown, E. (1986) J. Immunol. 136, 3793–3798
9. Wright, S., and Meyer, B. (1985) J. Exp. Med. 162, 762–767
10. Altieri, D., Agbanyo, F., Plescia, J., Ginsberg, M., Edgington, T., and Plow, E. (1990) J. Biol. Chem. 265, 12119–12122
11. Wright, S., Weicz, J., Huang, A., Levin, S., Silverstein, S., and Loike, J. (1988) Proc. Natl. Acad. Sci. U.S.A. 85, 7734–7738
12. Nathan, C., Scrimal, S., Farber, C., Sanchez, E., Kabbash, L., Asch, A., Gailit, J., and Wright, S. (1989) J. Cell Biol. 109, 1341–1349
13. Phillips, D., Charo, I., and Scarborough, R. (1991) Cell 65, 359–362
14. Smith, J., Ruggeri, Z., Kunicki, T., and Cheresh, D. (1990) J. Biol. Chem. 265, 12267–12271
15. Kloczewiak, M., Timmons, S., Lukas, T., and Hawiger, J. (1984) Biochemistry 23, 1767–1774
16. Gresham, H., and Brown, E. (1990) Clin. Res. 38, 480a (Abstr)
17. Posnett, D., McGrath, H., and Tam, J. (1988) J. Biol. Chem. 263, 1719–1725
18. Graham, I., Gresham, H., and Brown, E. (1989) J. Immunol. 142, 2352–2358
19. Gresham, H., Clement, L., Volanakis, J., and Brown, E. (1987) J. Immunol. 139, 4159–4166
20. Fok, K., Panzer-Knodle, S., Nicholson, N., Tjoeng, F., Feigen, L., and Adams, S. (1991) J. Peptide Protein Res. 38, 124–130
21. Gresham, H., Graham, I., Anderson, D., and Brown, E. (1991) J. Clin. Invest. 88, 588–597
22. Ruggeri, Z., Houghten, R., Russel, S., Zimmerman, T. (1986) Proc. Natl. Acad. Sci. U.S.A. 83, 5708–5712
23. D'Souza, S., Ginsberg, M., Burke, T., and Plow, E. (1990) J. Biol. Chem. 265, 3440–3446
24. Smith, C., Kishimoto, T., Abbassi, O., Hughes, B., Rothlein, R., Mcintire, L., Butcher, E., and Anderson, D. (1991) J. Clin. Invest. 87, 609–613

What is claimed is:
1. A hexapeptide having the following amino acid sequence

Lys Gly Ala Gly Asp Val.            [SEQ ID NO: 1]

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:1:

Lys  Gly  Ala  Gly  Asp  Val
    1                      5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

Ala  Lys  Gln  Ala  Gly  Asp  Val
    1                          5

( 2 ) INFORMATION FOR SEQ ID NO:3:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

Lys Gln Ala Gly Asp Val
   1               5

( 2 ) INFORMATION FOR SEQ ID NO:4:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

Gly Arg Gly Asp Ser Cys
   1               5

( 2 ) INFORMATION FOR SEQ ID NO:5:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:5:

Lys Gln Arg Gly Asp Val
   1               5

( 2 ) INFORMATION FOR SEQ ID NO:6:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:6:

Lys Gly Ala Leu Glu Val Ala
   1               5

( 2 ) INFORMATION FOR SEQ ID NO:7:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:7:

Gly Gln Gln His His Leu Gly Gly Ala Lys Gln Ala Gly Asp Val
   1               5                   10                  15

( 2 ) INFORMATION FOR SEQ ID NO:8:

( i ) SEQUENCE CHARACTERISTICS:
      ( A ) LENGTH: 12 amino acids
      ( B ) TYPE: amino acid -continued (D) TOPOLOGY: linear (ii) MOLECULE TYPE: peptide (xi) SEQUENCE DESCRIPTION: SEQ ID NO:8:

His His Leu Gly Gly Ala Lys Gly Ala Gly Asp Val
1               5                   10

(2) INFORMATION FOR SEQ ID NO:9:

(i) SEQUENCE CHARACTERISTICS:
(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO:9:

His His Leu Gly Gly Ala Lys Gln Arg Gly Asp Val
1               5                   10

(2) INFORMATION FOR SEQ ID NO:10:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:10:

Gly Arg Gly Asp Ser Pro Ala
1               5

(2) INFORMATION FOR SEQ ID NO:11:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO:11:

Gly His Gly Pro Gly Glu Gln Gln Leu Arg
1               5                   10